US00RE43655E

(19) United States
(12) Reissued Patent
Lebing et al.

(10) Patent Number: US RE43,655 E
(45) Date of Reissued Patent: *Sep. 11, 2012

(54) CHROMATOGRAPHIC METHOD FOR HIGH YIELD PURIFICATION AND VIRAL INACTIVATION OF ANTIBODIES

(75) Inventors: Wytold R. Lebing, Seattle, WA (US); Douglas C. Lee, Apex, NC (US); Klaus-Peter Radtke, Apex, NC (US); Scott A. Cook, Ballwin, MO (US); Hanns-Ingolf Paul, Leverkusen (DE); Patricia Alred, Downington, PA (US)

(73) Assignee: Bayer HealthCare LLC, Tarrytown, NY (US)

( * ) Notice: This patent is subject to a terminal disclaimer.

(21) Appl. No.: 11/873,878

(22) Filed: Oct. 17, 2007

Related U.S. Patent Documents

Reissue of:
(64) Patent No.: 6,955,917
Issued: Oct. 18, 2005
Appl. No.: 10/270,918
Filed: Oct. 15, 2002

U.S. Applications:
(63) Continuation-in-part of application No. 09/973,141, filed on Oct. 9, 2001, now abandoned, which is a continuation of application No. 09/270,724, filed on Mar. 17, 1999, now Pat. No. 6,307,028, which is a continuation-in-part of application No. 08/879,362, filed on Jun. 20, 1997, now Pat. No. 5,886,154.

(51) Int. Cl.
*C07K 16/00* (2006.01)
*C07K 1/14* (2006.01)
*C07K 1/30* (2006.01)
*C07K 1/36* (2006.01)

(52) U.S. Cl. ..... 530/387.1; 530/390.5; 530/412; 530/413; 530/417; 530/418; 530/419; 435/412; 435/413; 435/417; 435/418; 435/419

(58) Field of Classification Search ..... None
See application file for complete search history.

(56) References Cited

U.S. PATENT DOCUMENTS

| | | | | |
|---|---|---|---|---|
| 3,992,367 | A | 11/1976 | Plan et al. | |
| 4,136,094 | A | 1/1979 | Condie | |
| 4,156,681 | A | 5/1979 | Schneider et al. | |
| 4,396,608 | A | 8/1983 | Tenold | |
| 4,434,093 | A | 2/1984 | Zolton et al. | |
| 4,476,109 | A | 10/1984 | Kimura et al. | |
| 4,534,972 | A | 8/1985 | Lembach | |
| 4,540,573 | A | 9/1985 | Neurath et al. | |
| 4,639,513 | A | 1/1987 | Hou et al. | |
| 4,939,176 | A * | 7/1990 | Seng et al. | 530/388.15 |
| 4,983,722 | A | 1/1991 | Bloom et al. | |
| 5,075,425 | A | 12/1991 | Kotitschke et al. | |
| 5,110,910 | A * | 5/1992 | Tsav | 530/390.1 |
| 5,164,487 | A * | 11/1992 | Kothe et al. | 530/389.1 |
| 5,177,194 | A | 1/1993 | Sarno et al. | |
| 5,219,999 | A | 6/1993 | Suzuki et al. | |
| 5,258,177 | A * | 11/1993 | Uemura et al. | 424/176.1 |
| 5,410,025 | A | 4/1995 | Moller et al. | |
| 5,561,115 | A | 10/1996 | Tenold | |
| 5,886,154 | A * | 3/1999 | Lebing et al. | 530/390.1 |
| 6,307,028 | B1 * | 10/2001 | Lebing et al. | 530/390.1 |

FOREIGN PATENT DOCUMENTS

| | | |
|---|---|---|
| CA | 1201063 | 2/1986 |
| DE | 39 27 112 | 10/1990 |
| EP | 0 374 625 A2 | 12/1989 |
| EP | 0 440 483 A2 | 8/1991 |
| EP | 0 447 585 A1 | 9/1991 |

OTHER PUBLICATIONS

Lundblad et al (Vox Sang 60:75-81, 1991).*

Gelfand et al., "Safety and Tolerability of Increased Rate of Infusion of Intravenous Immunoglobulin G, 10% in Antibody-Deficient Patients", Journal of Clinical Immunology, vol. 26, No. 3, (2006), pp. 284-290.

Bussel et al., "Safety and Tolerability of a Novel Chromatography-Based Intravenous Immunoglobulin when Administered at a High Infusion Rate in Patients with Immune Thrombocytopenic Purpura", American Journal of Hematology, vol. 82, (2007), pp. 1-7.

Habeeb et al., "Preparation of Human Immunoglobulin By Caprylic Acid Precipitation", Preparative Biochemistry, vol. 14, No. 1 (1984), pp. 1-17.

Kistler et al., Large Scale Production of Human Plasma Fractions, (1962) p. 416.

Lebing et al., "A Highly Purified Antithrombin III Concentrate Prepared from Human Plasma Fraction IV-1 by Affinity Chromatography", Vox Sang, vol. 67, (1994), pp. 117-124.

Leibl et al., "Method for the Isolation of Biologically Active Monomeric Immunoglobulin A From a Plasma Fraction", Journal of Chromatography B, vol. 678, (1996), pp. 173-180.

McKinney et al., "A Simple Non-Chromatographic Procedure to Purify Immunoglobulins from Serum and Ascites Fluid", Journal of Immunological Methods, vol. 96, (1987), pp. 271-278.

(Continued)

*Primary Examiner* — Mary E Mosher
(74) *Attorney, Agent, or Firm* — Connolly Bove Lodge & Hutz, LLP

(57) ABSTRACT

An improved process for the purification of antibodies from human plasma or other sources is disclosed. The process involves suspension of the antibodies at pH 3.8 to 4.5 followed by addition of caprylic acid and a pH shift to pH 5.0 to 5.2. A precipitate of contaminating proteins, lipids and caprylate forms and is removed, while the majority of the antibodies remain in solution. Sodium caprylate is again added to a final concentration of not less than about 15 mM. This solution is incubated for 1 hour at 25° C. to affect viral inactivation. A precipitate (mainly caprylate) is removed and the clear solution is diluted with purified water to reduce ionic strength. Anion exchange chromatography using two different resins is utilized to obtain an exceptionally pure IgG with subclass distribution similar to the starting distribution. The method maximizes yield and produces a gamma globulin with greater than 99% purity. The resin columns used to obtain a high yield of IgG retain IgM and IgA. IgA and IgM may be eluted from these resins in high yield and purity.

12 Claims, 1 Drawing Sheet

OTHER PUBLICATIONS

Pejaudier et al., "Preparation of Human IgA as By-Product of Routine Fractionation", Vox Sang, vol. 23 (1972), pp. 165-175.

Prin et al., "Isoelectric Restriction of Human Immunoglobulin Isotypes", Biochemica et Biophysica Acta, vol. 1243, (1995), pp. 287-290.

Russo et al., "Purification of IgG Monoclonal Antibody by Caprylic Acid Precipitation", Journal of Immunological Methods, vol. 65, (1983), pp. 269-271.

Scopes, *Protein Purification: Principles and Practice:* "Separation by Precipitation", Ch. 3, (1985), pp. 39-66.

Steinbuch et al., "The Isolation of IgG from Mammalian Sera with the Aid of Caprylic Acid", Archives of Biochemistry and Biophysics, vol. 134 (1969), pp. 279-284.

Steinbuch, "Precipitation Methods in Plasma Fractionation", Vox Sang, vol. 23, (1972), pp. 92-106.

Steinbuch et al., "Preparation of an IgM and IgA Enriched Fraction for Clinical Use", Preparative Biochemistry, vol. 3, No. 4, (1973), pp. 363-373.

Surgenor et al., "Preparation and Properties of Serum and Plasma Proteins, XXXV", Vox Sang, vol. 5, (1960), pp. 272-296.

European Search Report for Appln 98110526.5 (mailed Oct. 8, 1998), 3 pgs.

EPO Opposition Division Decision Issued Jul. 11, 2007 Rejecting Opposition of EP 0893450, (7 pgs).

Opposition to EP 0893450 filed by Octapharma AG on Feb. 17, 2005, (12 pgs), (in German as filed and with English translation).

Reply to Opposition to EP0893450 filed by Bayer AG on Nov. 17, 2005, (5 pgs).

Comments prior to Oral Proceeding Held for Opposition to EP0893450 filed by Bayer AG on Mar. 16, 2007, (14 pgs).

Appeal Brief to Decision Rejecting Opposition filed by Octapharma AG on Nov. 12, 2007 (in German as filed and with English Translation), (3 pgs each).

Response to Opponent's Ground for Appeal of Opposition to EP 0893450 filed by Bayer AG on Jul. 8, 2008, (4 pgs).

Leibl et al (Journal of Chromatography B 678:173-180, Apr. 12, 1996).*

Lebing, Wytold R., et al., "A Highly Purified Antithrombin III Concentrate Prepared from Human Plasma Fraction IV-1 by Affinity Chromatography", *Vox Sang.* 67: 117-124. (1994).

* cited by examiner

CHROMATOGRAPHIC METHOD FOR HIGH YIELD PURIFICATION AND VIRAL INACTIVATION OF ANTIBODIES

Matter enclosed in heavy brackets [ ] appears in the original patent but forms no part of this reissue specification; matter printed in italics indicates the additions made by reissue.

This application is a continuation-in-part of U.S. application Ser. No. 09/973,141, filed Oct. 9, 2001 now abandoned, which is a continuation of U.S. application Ser. No. 09/270,724, filed Mar. 17, 1999 (now U.S. Pat. No. 6,307,028), which is a continuation-in-part of U.S. application Ser. No. 08/879,362 filed Jun. 20, 1997 (now U.S. Pat. No. 5,886,154).

BACKGROUND OF THE INVENTION

1. Field

This disclosure is generally concerned with protein purification and virus inactivation/removal and specifically with an improved process for the purification of gamma globulins from blood plasma and other sources.

2. Background

Carboxylic acids such as caprylic acid have been used in both preparation of plasma products (precipitation of proteins) and inactivation of viruses. See, for example, the summary of such use in Seng et al (1990).

Fractionation Using Caprylate:

During human immunoglobulin preparation caprylic acid is generally recognized as an effective precipitating agent for most plasma proteins at pH 4.8, so long as parameters such as temperature and ionic strength are optimized. Steinbuch et al. (1969) have described the precipitation of the bulk of the plasma proteins with caprylic acid without affecting IgG, ceruloplasmin and IgA. Steinbuch et al. isolated IgG from mammalian sera using caprylic acid and reported that extensive non-immunoglobulin precipitation was best obtained at slightly acidic pH, but not below pH 4.5. Plasma was diluted 2:1 with 0.06 M acetate buffer, pH 4.8, and then treated with 2.5 wt. % caprylate to initiate precipitation. Batch adsorption of the supernatant on DEAE-cellulose was used to clear additional impurities from the isolated IgG fraction. Later work by Steinbuch et al. showed the use of caprylic acid to precipitate most proteins and lipoproteins (other than the immunoglobulins) present in Cohn ethanol Fraction III. (Steinbuch et al., 1973).

The method of Steinbuch, supra, was applied to cell culture medium and ascites fluid from mice, using 0.86 wt. % caprylic acid for recovery of IgG. (Russo et al., 1983). The same method was applied to diluted human plasma using 2.16 wt. % caprylate. (Habeeb et al., 1984). Habeeb et al. followed the caprylic acid precipitation with fractionation on DEAE cellulose. The resulting plasma-derived IgG was free of aggregates, plasmin and plasminogen. In addition, the IgG obtained was low in anticomplement activity and relatively stable during storage.

As a result of these studies, scientists further developed several techniques for purifying IgA, IgG, alpha-1 acid glycoprotein, and prealbumin, concluding concurrently that the precipitation reaction was highly temperature and pH dependent. (Steinbuch et al., 1969; Steinbuch et al., 1973; see also Tenold, 1996).

As an example, IgA has been prepared as a routine fractionation by-product from Cohn fraction III, based on IgA solubility with caprylic acid present at pH 4.8. (Pejaudier et al., 1972). IgA isolated from cold ethanol Fraction III by DEAE-cellulose adsorption and elution was further purified by caprylic acid precipitation. Conditions for precipitation were 1.5-2% protein concentration, 0.9% sodium chloride, pH 5.0, 1.12 wt. % caprylic acid.

A two step purification of immunoglobulins from mammalian sera and ascites fluid has been described (McKinney et al., 1987). First albumin and other non-IgG proteins were precipitated using caprylic acid, and then ammonium sulfate was added to the supernatant to precipitate the IgG.

U.S. Pat. No. 5,164,487 to Kothe et al. (1992) concerns the use of caprylic acid for the manufacture of an intravenously tolerable IgG preparation free from aggregates, vaso-active substances and proteolytic enzymes. The method includes contacting the starting material containing IgG with 0.4% to 1.5% caprylic acid before chromatographic purification with an ion exchange or hydrophobic matrix.

Sodium caprylate has also been used to purify albumin. According to these methods, sodium caprylate is added to process plasma, and protects the albumin when the process stream is exposed to high temperatures. Extreme temperatures not only denature process stream globulins, but may also generate contaminant neo-antigens, (Schneider et al., 1979; Condie, 1979; see also Plan, 1976).

Tenold (1996) shows the use of caprylate as a partitioning agent for the isolation of albumin from Cohn fraction II+III or IV−I effluent. Again, the sodium caprylate is used to denature (and precipitate) globulins.

Viral Inactivation:

U.S. Pat. No. 4,939,176 to Seng et al. (1990) reports a process for inactivating viruses in solutions of biologically active proteins by contacting the solutions with caprylic acid. The preferred conditions recited for the process were pH 4 to pH 8, and 0.07% to 0.001% of the non-ionized form of caprylic acid.

Other methods of viral inactivation through the use of chemical agents are known. U.S. Pat. No. 4,540,573 to Neurath (1985) teaches the use of di-or tri-alkyl phosphates as antiviral agents. U.S. Pat. No. 4,534,972 to Lembach (1985) describes a method of rendering solutions of therapeutically or immunologically active proteins substantially free of infectious agents. In Lembach's method a solution of protein is contacted with a transition metal complex, e.g. copper phenanthroline, and a reducing agent to effect inactivation of viruses without substantially affecting the activity of the protein.

Anion Exchange Chromatography:

Bloom et al. (1991) gives an example of the use of anion exchange chromatography to purify antibody preparations. Their method includes contacting a solution containing antibodies and contaminating protein A with an anion exchange resin and then eluting the antibodies from the resin under conditions of increasing ionic strength.

Canadian Patent 1,201,063 to Friesen teaches the preparation of an IgG suitable for intravenous use by subjecting a plasma fraction to a two stage separation process using two different anion exchange resins. In each stage the buffer that is used to equilibrate the anion exchange resin is also used to elute the IgG-containing fraction from the resin.

A method of isolating a human IgG- and albumin-containing composition for intravenous administration has been described by Kimura et al. (1984). The method involves precipitation steps under controlled conditions of pH, ethanol concentration, ionic strength and temperature.

U.S. Pat. No. 5,410,025 to Moller et al. discloses a process of preparing a polyclonal chemically unmodified immunoglobulin preparation by anion exchange chromatography, where at least 5% by weight of all the immunoglobulin it contains is IgM.

SUMMARY OF THE INVENTION

The invention is an improved process for the purification of antibodies (especially of the IgG type) from human plasma and other sources. The process involves suspension of the antibodies at pH 3.8 to 4.5 followed by addition of caprylic acid (or other source of caprylate) and a pH shift to pH 5.0 to 5.2. A precipitate of contaminating proteins, lipids and caprylate forms and is removed, while the majority of the antibodies remain in solution. Sodium caprylate is again added to a final concentration of not less than about 15 mM. This solution is incubated under conditions sufficient to substantially reduce the titer of active virus (e.g., for 1 hour at 25° C.). A precipitate (mainly caprylate) is removed and the clear solution is diluted with purified water to reduce ionic strength. Anion exchange chromatography using two different resins is utilized to obtain an exceptionally pure antibody preparation with antibody subclass distribution similar to the starting distribution.

This method combines virus inactivation and removal as an integral part of the processing scheme and minimizes post virus treatment manipulation of the gamma globulin solution. By integrating virus treatment into the processing scheme, the method maximizes yield and produces a gamma globulin with greater than 99% purity.

Further, it has now been found that when two resin columns are used in series, such columns retain IgA and IgM respectively, and that subsequent elution of each column with a buffered solution having a conductivity at least about that of a 100 mM sodium chloride solution, frees the retained IgA and IgM fractions from,the columns in high yield and purity.

DETAILED DESCRIPTION OF THE INVENTION

Materials and Methods

Figure 1:
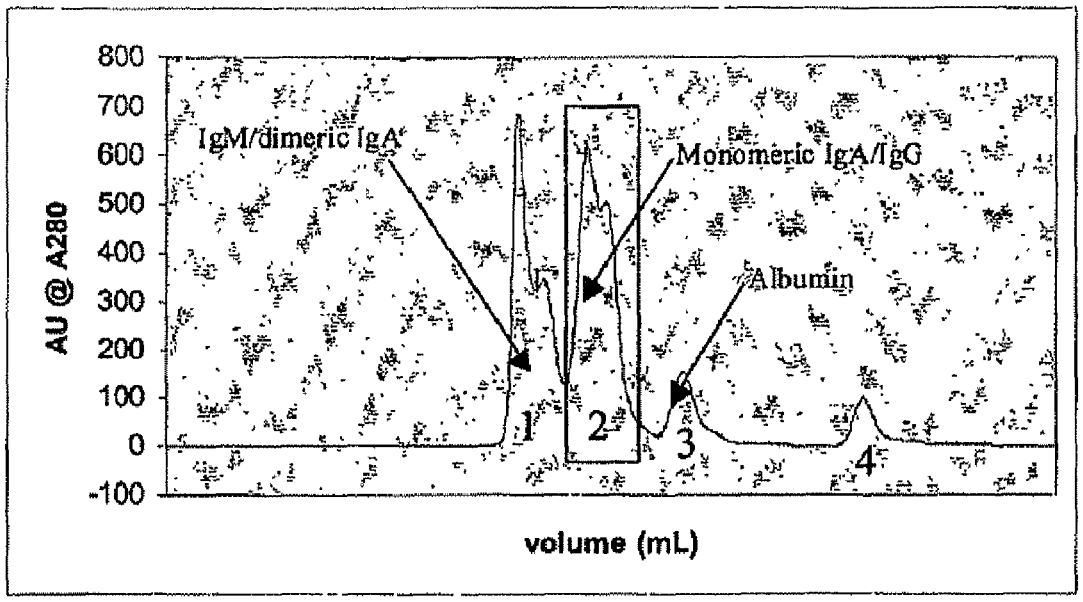
FIG. 1 shows a chromatogram showing that a size exclusion chromatographic step results in a purified fraction containing monomeric IgA contaminated with IgG. IgM, dimeric IgA, albumin and other contaminants were substantially eliminated by size exclusion chromatography. The box outline shows the fraction (peak 2) used for protein G SEPHAROSE experiments to remove IgG (see FIG. 2).

Adjustments of pH were done with 1 M acetic acid, 2 M acetic acid, 6% NaOH, 1 M NaOH, or 1 M HCl. Sodium caprylate stock solution was made by dissolving 30% sodium caprylate in water for injection by mixing. Human plasma fraction II+III was produced as described by Lebing et al. (1994). All reagents were USP grade or better. Nephelometry was done using a Beckman Array 360 Nephelometer and Beckman kits. Analytical HPLC was done using HP 1050 systems with Tosohaas G3000SW and G4000SW SEC columns. Protein was determined using the Biuret method.

The procedure is robust and simple. The process begins by redissolving precipitated antibodies in purified water at a pH around 4.2. In practice, increasing the amount of water per unit of paste results in increased yield. However, when processing hundreds of kilograms of paste it is practical to sacrifice some yield in order to keep vessel and column scale within workable limits. Yields across the dissolving step, viral inactivation, and chromatography are relatively important because immunoglobulin demand generally far exceeds supply.

Inactivation of enveloped viruses requires that the bulk of the pH sensitive precipitate be removed prior to the inactivation step. In addition, sodium caprylate content should be 15-60 mM during the 25° C. hold to achieve complete inactivation of enveloped viruses. Virus inactivation studies have confirmed that caprylate at 16 mM or 18 mM inactivates over 4 log units of Bovine Viral Diarrhea Virus and Pseudorabies virus (both enveloped viruses) in 30 minutes at 24° C. This additional chemical virus inactivation supplements the virus inactvation of a pH 4.25 hold step also incorporated into the manufacturing process.

The primary steps of the process are defined as

1) Suspending a composition containing precipitated immunoglobulins in purified water for injection (WFI) at 5° C. with vigorous mixing. In a preferred embodiment fraction II+III paste is used, but other sources may also be used, such as ascites fluid, tissue culture media containing antibodies, other human plasma fractions, or animal plasma fractions.
2) Dissolving immunoglobulins into solution by lowering the mixture to pH 3.8 to 4.5, preferably 4.2, by the addition of acid, preferably acetic acid, with further vigorous mixing.
3) Adding a source of caprylate ions (e.g., 40% w/v sodium caprylate in water) to a final concentration of 15 mM to 25 mM, preferably 20 mM, and adjusting the pH up to 5.0 to 5.2, preferably 5.1, with a base (such as 1 M NaOH).
4) Removal of precipitated proteins, lipids, and caprylate by filtration at ambient temperature (e.g., 5-25° C.). The filtration requires addition of filter aid (for example, in this case the filter aid is 2% to 5% diatomaceous earth). The solution is filtered using normal flow filtration. This step results in significant reduction of non-enveloped virus. Centrifugation may be substituted for filtration.
5) Addition of further caprylate to adjust the concentration back up to about 15 mM to about 60 mM, preferably 20 mM, while pH is held at 5.0-5.2, preferably 5.1, by the addition of acid (e.g. 1 M acetic acid).
6) The temperature is increased to about 25-35° C., preferably 25° C., and held for a period of about 15 minutes to about 6 hours, preferably about one hour. Longer incubation times may be used with some sacrifice in yield. A precipitate of principally caprylate and some additional protein is formed during this step.
7) Filter aid (diatomaceous earth) is added and precipitate is removed by normal flow filtration. Enveloped viruses are inactivated by the caprylate hold, and non-enveloped viruses are captured on the filter pad.
8) The clarified solution is diluted with purified water to reduce conductivity between 1-8 mS/cm, preferably less than 5 mS/cm.
9) Passing the solution through two anion exchange chromatography columns linked in series. The anion exchangers are chosen for ability to remove IgA, IgM, albumin and other remaining protein impurities. After loading, the columns are washed with equilibration buffer. The flow through and wash fraction are collected as purified IgG. Both columns are equilibrated with the same buffer and at the same pH.

Several anion exchange resin combinations may be utilized depending on selectivity of the resins. The anion exchange resins are chosen for their ability to selectively remove the impurities found in alcohol/pH precipitated plasma fractions. In developing this method, satisfactory purifications were obtained with combinations of PHARMACIA BIOTECH Q & ANX resins and E. MERCK TMAE FRACTOGEL.

Conditions described for the chromatography generally range from pH 5.0 to 5.2. At pH<5.0 impurities pass through the columns. At pH>5.2 yield is sacrificed. Ionic strength during the chromatography is relatively important because reduced purity is observed as ionic strength is increased during the chromatography.

In preferred embodiments, the solution is applied directly to the first anion exchanger which has been equilibrated with 20 mM sodium acetate at pH 5.1. This is followed by applying the non-binding fraction (the flow through) from the first anion exchange column directly onto the second anion exchange column. This column has also been equilibrated with 20 mM acetate buffer at pH 5.1. The protein solution is typically loaded onto the first column at a ratio of 50-110 mg IgG/ml packed resin. The protein solution is typically loaded onto the second column at a ratio of 75-95 mg IgG/ml packed resin. The protein to resin ratios can also be adjusted beyond these limits, but doing so will have an impact on yield and purity. The protein solution is followed by approximately 2 column volumes of the equilibration buffer, which washes any non-bound IgG off of the columns. The unbound fraction is collected as highly purified IgG, which is then diafiltered and the protein is concentrated to final formulation values.

The preferred conditions for final product are chosen based on patents held by this manufacturer. These conditions (low pH and low salt) would, in theory, benefit any IgG product. The collected protein is adjusted to pH 4.2. It is ultrafiltered to a concentration of approximately 5% (w/v). It is then diafiltered with purified water.

The purified IgG is either concentrated to a stable liquid formulation (as described by Tenold, 1983) or other appropriate final formulation (e.g. a freeze dried formulation). For a liquid formulation the purified IgG is concentrated to yield either 5% or 10% IgG (w/v) following sterile filtration. Prior to filtration, the pH is adjusted to 3.80 to 4.25 and maltose or glycine is added to adjust osmolarity to be compatible for intravenous injection. The sterile bulk is then held for not less than 21 days to reduce anti-complement activity and to inactivate enveloped viruses.

It was found that IgA and IgM could be obtained from the resin columns at significant yield and purity. IgA is obtained by eluting the first anion resin exchange column with a buffered solution having at least the conductivity of a 100 mM sodium chloride solution. The preferred range is believed to be in the conductivity range of about 100 mM to 250 mM sodium chloride. However, a significant yield has been obtained with elution by 1 Molar sodium chloride. IgM is obtained in about 90% purity from the second anion resin column with the same procedure. The products are separated from the eluate in the customary manner.

In one embodiment of the invention, IgA from the bound fraction of the first anion exchange column of the IgG purification process, as described above, is further purified by size exclusion chromatography. The first anion exchange eluate (eluted using a buffered solution having at least the conductivity of a 100 mM sodium chloride solution) was applied to a gel filtration column. The elution profile had five protein peaks identified by immunonephelometry as IgM, dimeric IgA, monomeric IgA, IgG, and albumin, respectively. Rechromatography of the monomeric IgA peak on a gel filtration column resulted in one major protein peak and two small shoulders containing monomeric IgA, dimeric IgA, and IgG, respectively. Fractions containing monomeric IgA were pooled, eliminating those that contained dimeric IgA and IgG.

Several preparations of highly purified IgA migrated as a 160,000 Da band on non-reduced polyacrylamide gels. A minor band of slightly lower molecular weight was interpreted as a form having a different glycosylation pattern. The identity of IgA was further confirmed by SDS-PAGE and western blots comparing non-reduced and reduced forms of IgG, IgM, and IgA.

IgA dissociated into two fragments of 20,000 Da and 60,000 Da on a reducing SDS-PAGE, consistent with the molecular weight of the IgA light chain and the α-heavy chain of the molecule. In western blots, IgA, but not IgM or IgG, was detected by alkaline phosphatase-labeled, antihuman IgA under non-reducing and reducing conditions. Endotoxin levels in the final preparations of IgA were determined to be <0.05 U/ml. This value was deemed acceptable for in vivo experiments based on the release criterion for intravenously administered immunoglobulins (0.5 U/ml).

In yet another embodiment of the invention, IgA from a high salt eluate of the first anion exchange column is further purified using size exclusion chromatography and subsequent protein G affinity chromatography. The purified IgA can also be passed through a nanofiltration device, demonstrating a pathogen clearance mechanism for the IgA preparation.

The size exclusion chromatographic step results in a purified fraction containing monomeric IgA contaminated with IgG. IgM, dimeric IgA, albumin and other contaminants were substantially eliminated by size exclusion chromatography. See FIG. 1 and Table 2 below. The contaminating IgG was substantially eliminated by a protein affinity chromatographic step, as determined by immunonephelometry. See FIG. 2 and Table 4. SDS-PAGE confirmed that this process was capable of yielding IgA in the flow-through fraction of greater than 95% purity.

Purified IgA was also subjected to nanofiltration, demonstrating feasibility of this method for viral clearance using IgA prepared according to the methods of the present invention.

As used herein, percent values for concentrations are determined on a weight/volume basis.

As used herein, to substantially reduce the titer of active virus means to reduce the titer of active virus by at least about 2 log units, more preferably at least about 3 log units, and most preferably at least about 4 log units.

As used herein, substantially all of a protein means at least about 90% of the protein. Substantially none of a protein means less than about 5% of the protein.

EXAMPLE 1

Purification of IgG from Cohn Fraction II+III Paste

Fraction II+III paste was solubilized in 12 volumes of 5° C. purified water. The mixture pH was adjusted to pH 4.2 with acetic acid, and mixed for 1 hour. This step put the IgG into solution.

The mixture pH was then adjusted up to pH 5.2 with NaOH and sodium caprylate (the "pH swing"). Proteins and lipids were precipitated. The mixture was clarified by filtration to remove precipitate which would interfere with virus inactivation. The caprylate concentration was adjusted to 20 mM at pH 5.1, and the mixture was incubated for 1 hour at 25° C. to effect enveloped virus inactivation.

The mixture was filtered to produce a clear solution for chromatography. The solution conductivity was adjusted to between 2.0 and 3.0 mS/cm using purified water. The pH of the solution was adjusted to 5.0 to 5.2 following the conductivity adjustment.

The solution was then applied directly to two anion exchange columns (a strong anion exchanger followed by a weak anion exchanger). The two columns were linked in series. The IgG flowed through the column while impurities (including the caprylate) were bound to the two anion columns.

The pH of the collected flow through from the chromatography was adjusted to 3.8 to 4.0 using acetic acid. It was diafiltered with seven exchanges of buffer (purified water). It was then concentrated and final formulated at pH 4.2.

The overall yield from paste dissolving to final product was 69% (see the table). This was a significant improvement over the prior process yield using the alcohol process wash (48%).

TABLE 1

Yield Summary

| Process | Starting Amount | Recovery g/liter plasma | Recovery % Process |
|---|---|---|---|
| New Chromatography Process | 7.0 kg | | |
| Starting II + III paste | | 6.5 | |
| Post CIM Treatment | | 5.45 | 84% |
| Post Chromatography | | 5.0 | 77% |
| Final Container | | 4.5 | 69% |
| Old Production Process | 7.0 kg | | |
| Starting II + III paste | | 6.5 | |
| Effluent III | | | |
| Filtrate III | | | |
| Final Container | | 3.1 | 48% |

EXAMPLE 2

Purification of IgG from Cell Culture Medium

Cell line growth media containing secreted monoclonal antibodies is first adjusted to the proper pH and conductivity. This accomplished by diafiltering against purified water while adjusting the pH to 4.2 with acetic acid. The conductivity should be less than 1.0 mS.

Purification of the monoclonal antibody is achieved by following the steps above. The purified monoclonal antibody is then concentrated and final formulated to a pH of 4.2 using glycine, maltose, or other suitable excipients. By formulating at pH 4.2 a liquid solution stable for 2 years at 5° C. can be achieved. This is highly desirable from a commercial standpoint.

EXAMPLE 3

Recovery of IgA and IgM from Cohn Fraction II+III Paste

The process described in Example 1 was followed and IgG obtained in high yield and purity as described. However, subsequent experimentation revealed that IgA could be eluated from the first anion exchange resin column with a high concentration salt solution, and that IgM could be eluated from the second anion exchange resin column with a similar high concentration salt solution. It is believed that a buffered solution having at least the conductivity of 100 mM sodium chloride would provide similar results. An eluant would have a preferred range of conductivity equivalent to that of 100 to 250 mM sodium chloride. The first anion exchange column is preferably a strong anion exchange resin such as Pharmacia Biotech Q and the second anion exchange column is preferably a weak anion exchange resin such as Pharmacia Biotech ANX.

EXAMPLE 4

Purification of IgA by Size Exclusion Chromatography

Monomeric IgA from human plasma was purified by two consecutive size-exclusion chromatography steps on SUPERDEX 200 using a BIOLOGIC chromatography station (BioRad, Richmond, Calif.). The high-salt eluate of the Q-SEPHAROSE chromatography step (see Example 3) was used as starting material and contained 13 mg/ml of IgA having a purity of 45% by immunonephelometry and total protein determination.

Briefly, 20-ml of starting material were applied to a prepacked, 2-liter 200 XK 50/100 column (5 cm×93 cm, Pharmacia, Upsala, Sweden) and run at 10 ml/min in Tris Buffered Saline (TES) buffer (Sigma, St. Louis, Mo.). Fractions were analyzed by nephelometry, SDS-PAGE, and size exclusion-FPLC, Fractions positive for monomeric IgA were pooled, concentrated to a final volume of 10 ml with an AMICON concentration chamber (YM 10 membrane, room temperature)(Amicon, Beverly, Mass.), and reapplied to the SUPERDEX 200 column using the same running conditions as in the first run. The final product was formulated in 0.2 M glycine, pH 4.25 and sterile filtered using a 0.2 μm membrane.

EXAMPLE 5

Characterization of IgA Purified by Size Exclusion Chromatography

Immunonephelometry was used to quantify IgA in different fractions from the purification process of Example 4. A BECKMAN COULTER ARRAY 360 System was used along with goat anti-human IgA as per manufacture directions (Beckman Coulter, Brea, Calif.). A reference plasma was used for calibration.

SDS-polyacrylamide gel electrophoresis (reducing and non-reducing) was performed with a PHAST System (Pharmacia, Upsala, Sweden), precast 4-15% gradient gels, and SDS buffer strips (1% SDS). Samples were reduced with 1% 2-mercaptoethanol (Sigma, St. Louis, Mo.) and heated at 100° C. for 1 min. Gels were developed by Fast Coomassie staining using technique file No. 200 (Pharmacia).

Purified monomeric IgA was analyzed by size exclusion FPLC using a SUPERDEX 200 HR 10/30 column (1 cm×30 cm, Pharmacia, Upsala, Sweden) and a BIOLOGIC chromatography system (BioRad, Richmond, Calif.). Fifty microliters of final product were applied to the column and run at 0.75 ml/min in TBS buffer (Sigma, St. Louis, Mo.).

Protein bands were transferred from SDS-PAGE to nitrocellulose membranes using the PHAST System transfer kit. IgA was detected using alkaline phosphatase-labeled goat anti human IgA antibody (Jackson Immuno Research, West Grove, Pa.). [Bayer Notebook No. CRB 9926-845 pp. 22-30]

Analysis of purified IgA samples was carried out using LAL COATEST Endotoxin Assay (Chomogenix, Mölndol, Sweden).

Total protein concentration was determined by $A_{280}$ using an extinction coefficient of 1 for protein solutions and 1.37 for IgA.

EXAMPLE 6

Purification of IgA by Size Exclusion and Affinity Chromatography

Q-SEPHAROSE eluates as described in Example 3 (BIOTECH Q) were pooled and determined to have a final volume of 41.86 L. The IgA concentration in the pool was determined to be 4.95 g/L by nephelometry.

The pooled eluate was applied over a 2×0.5-$m^2$ PELLICON 30K (Millipore P2B030A05; Millipore Corporation, Bedford, Mass.) membrane and concentrated 2.5-fold from an $A_{280}$ of 11.94 AU/ml (41.86 L) to an $A_{280}$ of 29.30 AU/ml (16.36 L). This target $A_{280}$ was determined by comparison to the Q-SEPHAROSE elute lot used as described in Example 4 above.

Size Exclusion Chromatography

Nephelometry testing indicated that the concentrated final pool had an [IgA]=11.68 g/L, a 2.4-fold increase over the 4.95 g/L in the unconcentrated pool. Seventy-three ml of pooled Q-SEPHAROSE eluate was loaded on a 10 cm×93 cm SUPERDEX 200 column equilibrated in TBS, pH 7.4. The column was isocratically eluted with TBS at 26.75 cm/hr and fractions collected manually in sterile bottles. These fractions were analyzed by immunonephelometry. The chromatogram is shown in FIG. 1.

As shown in FIG. 1, peak 1 typically contained IgM and dimeric IgA, peak 2 contained monomeric IgA and IgG, and peak 3 contained albumin. Peak 4 absorbed at $A_{280}$ but had no detectable levels of IgG, IgA, IgM, or albumin by immunonephelometry. Peak 2 contained IgA and IgG (outlined with a rectangle on the chromatogram of FIG. 1). This fraction was used for protein G-SEPHAROSE experiments for removal of the IgG. By immunonephelometry, peak 2 yielded 500 mg of IgA, corresponding to a yield of 59%. The amounts of each protein, as determined by nephelometry, were as indicated in Table 2. Table 3 below reports the various mass balances and IgA yield.

TABLE 2

Immunonephelometry of SUPERDEX 200 peaks

| Fraction | Albumin (mg) | IgA (mg) | IgG (mg) | IgM (mg) |
|---|---|---|---|---|
| Load | 109 | 862 | 320 | 131 |
| 1 | 0 | 437 | 49 | 120 |
| 2 | 0 | 376 | 232 | 0 |
| 3 | 97 | 0 | 4.9 | 0 |
| 4 | 0 | 0 | 0 | 0 |

TABLE 3

Mass balances and IgA yield

| | A280 | IgG* | IgA* | IgM* | Albumin* |
|---|---|---|---|---|---|
| Mass Balance | 8% | 89% | 94% | 89% | 92% |
| Yield | N.A. | N.A. | 59% | N.A. | N.A. |

*concentrations determined by immunonephelometry

Protein G-Sepharose Affinity Chromatography

Figure 2:
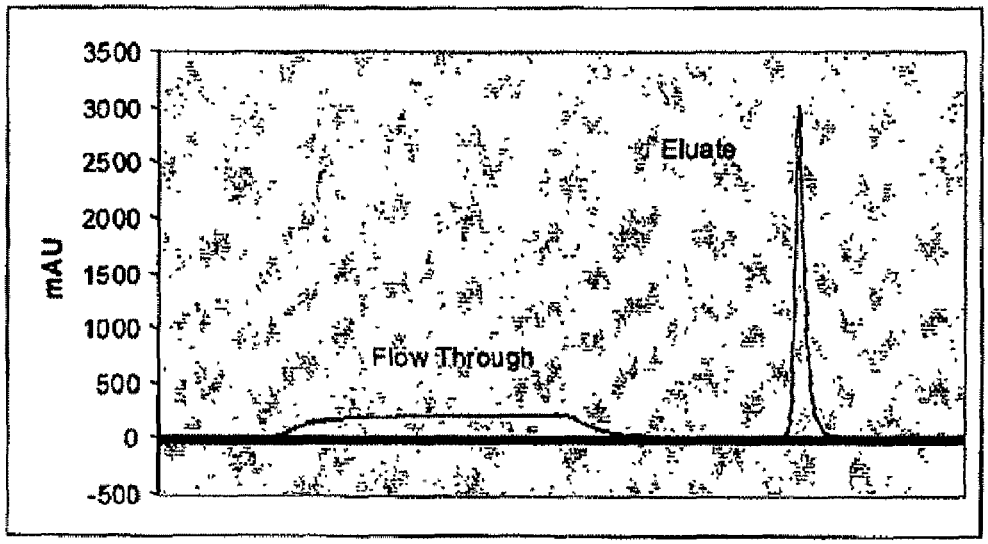
FIG. 2 shows a chromatograph of the protein G affinity chromatography of peak 2 as illustrated in FIG. 1.

For further purification of IgA, a PHARMACIA PROTEIN G-SEPHAROSE FAST FLOW column (0.5 cm×5.9 cm) was equilibrated with EQ buffer (1×TBS; 20 mM Tris-HCl, 0.9% NaCl, pH 7.4) and the sample (SUPERDEX 200 IgA/IgG peak) was loaded in the same EQ Buffer. The column was run at a linear velocity of 200 cm/hr. The flow through was pooled for analysis. After unbound sample was washed out with EQ buffer, bound protein was eluted using 100 mM glycine, pH 2.5. The eluate was also pooled for analysis. The resin was then re-equilibrated with consecutive washes using 5×TBS followed by 1×TBS. The $A_{280}$ chromatogram trace for the PHARMACIA PROTEIN G-SEPHAROSE FAST FLOW chromatography is shown in FIG. 2.

Analysis of the load, flow through and eluate fractions included $A_{280}$ measurements, nephelometry and SDS-PAGE, with results described below.

TABLE 4

$A_{280}$ and Nephelometry of PROTEIN G-SEPHAROSE Fractions

| Protein G-SEPHAROSE Fraction Description | Volume (ml) | $A_{280}$/mL (AU/ml) | IgA Nephel. (mg/ml) | IgG Nephel. (mg/ml) |
|---|---|---|---|---|
| Sample Load | 33.14 | 1.12 | 0.58 | 0.33 |
| Flow-Through | 51.0 | 0.41 | 0.35 | <0.01 |
| Eluate | 10.0 | 1.42 | 0.01 | 0.77 |

It is clear that the flow through fraction contains IgA with little or no IgG present. The data for the eluate fraction show that the PROTEIN G-SEPHAROSE resin binds almost exclusively IgG and minimal IgA. Accordingly, protein G is an effective means of separating IgA and IgG. SDS-PAGE analysis supported these findings. IgA was found to be >95% pure by reducing SDS-PAGE.

Mass balance for the PROTEIN G-SEPHAROSE FAST FLOW chromatography was calculated for both IgA and IgG using both $A_{280}$ measurements and nephelometry. Overall mass balance on the basis of $A_{280}$ was 94.6%. On the basis of nephelometry, IgA mass balance was 93.8%, while IgG mass balance was 75.2%. IgA yield across this step was 93.2%.

EXAMPLE 7

Nanofiltration of Purified IgA

IgA generated according to Example 5 was used to demonstrate feasibility of viral clearance using nanofiltration technology. Vmax trials using VIRESOLVE NFP (Millipore Corporation, Bedford, Mass.) were performed to demonstrate feasibility in a non-virally challenged system. Two IgA concentrations were used, 0.373 mg/ml and 2.24 mg/ml (both in TBS, pH 7.5; equivalent buffer conditions for the Protein G-SEPHAROSE flow thru fractions which contain >95% pure IgA). Both IgA concentrations demonstrated 98% IgA recovery based on $A_{280}$. Using flow rate, the data suggested to process 100 L in 2 hours, 4×10" cartridges would be required for IgA at 0.373 mg/ml and 10×10" cartridges needed for IgA at 2.24 mg/ml.

DISCUSSION

Immunoglobulins precipitate with the II+III fraction during the Cohn alcohol fractionation. Precipitation relies on the overall charge of the protein surface and its interaction with the solvent. Exacting salt, alcohol, and pH ranges can somewhat limit the range at which proteins precipitate. However, most proteins precipitate across a wide range of pH and alcohol concentration (as much as 1.5 pH units and 10% alcohol). Thus precipitation ranges of proteins tend to overlap. All three major immunoglobulin types, IgG, IgA, and IgM, are coprecipitated due to the similarity of their isoelectric points. Further separation of the immunoglobulin is complicated by this similarity. Therefore, production schemes which utilize precipitation require that a significant amount of the IgG is coprecipitated with the IgA and IgM.

In addition to yield decrease, classical precipitation requires the use of ethanol. Because ethanol destabilizes the proteins, reduced temperatures (typically −5° C.) are required during processing to increase protein stability. Chromatography can avoid problems of protein denaturation that commonly arise in precipitation strategies. The protein chromatography steps generally can be done under conditions which favor protein stability. Another disadvantage of ethanol fractionation is that due to its chemical nature alcohol is a potential explosion hazard which requires explosion proof facilities and special handling protocols. This fact significantly increases the cost of the fractionation process, a drawback which does not exist with conventional chromatographic methods.

Ion exchange chromatography takes advantage of surface distribution and charge density on both the protein and the ion exchange media. The anion exchange resin presents a positively charged surface. The charge density is specific to the resin and generally is independent of pH (within the working range of the resin). A typical anion exchanger will bind proteins which have a net negative charge (i.e. when the pH of the solution is above the isoelectric point of the protein). In reality, the surface of a protein does not present a singular charge; rather it is a mosaic of positive, negative, and neutral charges. Surface structure is specific to a given protein and will be affected by solution conditions such as ionic strength and pH. This uniqueness can be exploited to establish specific conditions where individual proteins will bind or release from the anion exchange resin. By establishing these conditions, proteins with only slightly differing surface or charge properties can be effectively separated with high yield (>95%).

Improvements in the structure of chromatography resin supports have made large scale chromatography a practical alternative to more conventional purification methods. Rigid resins allow large volumes to be processed rapidly (<5 hours), and high ligand density gives the increased capacity necessary for large volume processing. These factors coupled with high yields, product purity and process simplicity favor the use of chromatography in large scale manufacturing.

CONCLUSION

The chromatography process described herein takes advantage of the high specificity of chromatography resins. Two anion exchangers are used to selectively remove protein contaminants and the viral inactivation agent. The resulting product is of >99% purity when assayed by either nephelometry or size exclusion chromatography (SEC-HPLC).

The process is also designed to minimize loss of IgG. Virus inactivation and removal has been carefully integrated into the dissolving and chromatography steps, therefore increasing the process efficiency. The overall yield from paste dissolving to final product is 69% (see the table). This is a significant improvement over the current process yield using the alcohol process wash (48%). While the process minimizes the loss of IgG, it also provides a new and efficient method to obtain IgM and IgA in good yield and purity.

The process was performed on human Cohn fraction II+III paste in example 1. However, it is anticipated that the process may be used with equivalent results on plasma fractions isolated from non-human animals as well.

The above examples are intended to illustrate the invention and it is thought variations will occur to those skilled in the art. Accordingly, it is intended that the scope of the invention should be limited only by the claims below.

REFERENCES

Bloom, James W., et al., Removal of protein A from antibody preparations, U.S. Pat. No. 4,983,722 (Jan. 8, 1991).

Condie, Richard M., Preparation of intravenous human and animal gamma globulins and isolation of albumin, U.S. Pat. No. 4,136,094 (1979).

Friesen, Albert D., Process for preparing purified immune globulin (IgG), Canadian Patent 1,201,063 (1986).

Habeeb, A. F. S. A., et al., Preparation of human immunoglobulin by caprylic acid precipitation, Prep. Biochem. 14: 1-17 (1984).

Kimura, Tokosuke, et al., Method of preparing gamma globulin suitable for intravenous administration, U.S. Pat. No. 4,476,109 (1984).

Kothe, Norbert, et al., Manufacturing intravenous tolerable immunoglobulin-G preparation, U.S. Pat. No. 5,164,487 (1992).

Lebing, Wytold R., et al., A highly purified antithrombin III concentrate prepared from human plasma fraction IV-1 by affinity chromatography, Vox Sang. 67: 117-24 (1994).

Lembach, Kenneth J., Protein compositions substantially free from infectious agents, U.S. Pat. No. 4,534,972 (1985).

McKinney, Michella M., et al., A simple, non-chromatographic procedure to purify immunoglobulins from serum and ascites fluid, J. Immunol. Meth. 96: 271-78 (1987).

Moller, et al., Unmodified Intravenously Administered Immunoglobulin Preparations Containing Immunoglobulin M and/or A, U.S. Pat. No. 5,410,025 (1995).

Neurath, Alexander R., et al., Undenatured virus-free biologically active protein derivatives, U.S. Pat. No. 4,540,573 (1985).

Pajaudier, L., et al., Preparation of human IgA as by-product of routine fractionation, Vox. Sang. 23: 165-75 (1972).

Plan, Robert A. M., et al., Process for the preparation of purified albumin by thermocoagulation and albumin obtained by said process, U.S. Pat. No. 3,992,367 (1976).

Russo, C., et al., Immunol. Meth. 65: 269-71 (1983).

Schneider, et al., Process for isolating albumin from the blood, U.S. Pat. No. 4,156,681 (1979).

Seng, Richard L., et al., Viral inactivation process, U.S. Pat. No. 4,939,176 (1990).

Steinbuch, M., et al., The isolation of IgG from mammalian sera with the aid of caprylic acid, Arch. Biochem. Biophys. 134: 279-94 (1969).

Steinbuch, M., et al., Preparation of an IgM and IgA enriched fraction for clinical use, Prep. Biochem. 3: 363-73 (1973).

Tenold, Robert, Intravenously injectable immune serum globulin, U.S. Pat. No. 4,396,608 (1983).

Tenold, Robert, Low temperature albumin fractionation using sodium caprylate as a partitioning agent, U.S. Pat. No. 5,561,115 (Oct. 1, 1996).

What is claimed is:

1. A method of obtaining purified IgA from a solution comprising monomeric IgA at from about 8 mg/ml to about 15 mg/ml and at from about 35% to about 55% purity, and dimeric IgA IgM, IgG, and albumin contaminants, the method comprising:

passing the solution over a size exclusion chromatographic resin;

collecting a first IgA-containing fraction substantially free of contaminants other than IgG and dimeric IgA;

passing the first IgA-containing fraction over a protein G-affinity chromatographic resin;

collecting a second IgA-containing fraction.

2. A method of preparing a purified IgA preparation from a starting solution comprising immunoglobulins and other substances, the method comprising:

adjusting the pH of the starting material to allow formation of an intermediate solution comprising dissolved immunoglobulins;

adjusting the intermediate solution to conditions of pH, temperature, and caprylate concentration such that a first precipitate and a first supernatant comprising immunoglobulins are formed;

separating the first supernatant from the first precipitate;

incubating the first supernatant under conditions of time, pH, temperature and caprylate concentration such that a second precipitate and a second supernatant comprising immunoglobulins are formed;

separating the second supernatant from the second precipitate;

contacting the second supernatant with an anion exchange resin under conditions of pH and ionic strength such that IgA binds to the anion exchange resin;

separating a fraction containing at least a portion of contaminants and immunoglobulins other than IgA from the IgA bound to the anion exchange resin;

eluting IgA from the first anion exchange resin column with a buffered solution having a conductivity in the range of that found in a solution of at least 100 mM sodium chloride;

collecting the eluted IgA to obtain a purified, IgA preparation;

passing the IgA preparation over a size exclusion chromatographic resin;

collecting a first IgA-containing fraction substantially free of contaminants other than IgG and dimeric IgA;

passing the first IgA-containing fraction over a protein G-affinity chromatographic resin; and collecting a second IgA-containing fraction.

3. A method of claim 2, wherein the first IgA-containing fraction is substantially free of contaminants other than IgG.

4. A method of claim 2, wherein the starting solution comprises IgA at from about 35% to about 55%.

5. A method of claim 2, wherein the starting solution comprises dimeric IgA and the second IgA-containing fraction is substantially free of dimeric IgA.

6. A method of claim 2, wherein the starting solution comprises from about 8 mg/ml to about 15 mg/ml IgA.

7. A method of preparing a purified IgA preparation from a starting solution comprising immunoglobulins and other substances, the method comprising the steps of:

a) adjusting the pH of the starting material to be within a range of from about 3.8 to about 4.5 to form an intermediate solution comprising dissolved immunoglobulins;

b) adjusting the intermediate solution of step a) to conditions of pH, temperature, and caprylate concentration such that a first precipitate and a first supernatant comprising immunoglobulins are formed, wherein the conditions under which the first precipitate and first supernatant form comprise a pH within a range of from about 5.0 to about 5.2 and a caprylate concentration within a range of from about 15 mM to about 25 mM;

c) separating the first supernatant from the first precipitate;

d) incubating the first supernatant under conditions of time, pH, temperature and caprylate concentration such that a second precipitate and a second supernatant comprising immunoglobulins are formed, wherein the conditions under which the second precipitate and second supernatant form comprise a pH within a range of about 5.0 to about 5.2 and a caprylate concentration within a range of about 15 mM to about 40 mM;

e) separating the second supernatant from the second precipitate;

f) contacting the second supernatant with a first anion exchange resin under conditions of pH and ionic strength such that substantially no IgG or IgM is bound to the first resin but IgA and other substances are bound to the first resin;

g) separating a fraction containing substantially all of the immunoglobulins other than IgA from the result of step f);

h) eluting IgA from the first anion exchange resin column with a buffered solution having a conductivity in the range of that found in a solution of at least 100 mM sodium chloride;

i) separating the eluted IgA to obtain a purified IgA preparation;

j) passing the IgA preparation over a size exclusion chromatographic resin;

k) collecting a first IgA-containing fraction substantially free of contaminants other than IgG and dimeric IgA;

l) passing the first IgA-containing fraction over a protein G-affinity chromatographic resin; and m) collecting a second IgA-containing fraction.

*8. A method of preparing a purified, virally inactivated antibody preparation from a starting solution comprising antibodies and other substances at an initial pH, the method comprising the steps of:*

*(a) adding sodium caprylate to the starting solution to obtain a sodium caprylate concentration within a range of from about 15 mM to about 25 mM and adjusting the pH to within a range of from about 5.0 to about 5.2 to form a precipitate and a supernatant solution comprising antibodies, and*

*(b) incubating the supernatant solution under conditions of time, pH, temperature, and caprylate ion concentration to inactivate substantially all enveloped viruses to produce a purified, virally inactivated antibody preparation.*

*9. A method of preparing a purified, virally inactivated antibody preparation from a starting solution comprising antibodies and other substances at an initial pH, the method comprising the steps of:*

*(a) adding sodium caprylate to the starting solution and adjusting the pH to form a precipitate and a supernatant solution comprising antibodies, and*

*(b) incubating the supernatant solution under conditions of time, pH, temperature, and caprylate ion concentration to inactivate substantially all enveloped viruses to produce a purified, virally inactivated antibody preparation, wherein the conditions under which substantially all enveloped viruses are inactivated comprise a temperature of about 25-35° C., a period of time of about 15 minutes to about 6 hours, pH of the supernatant solution of 5.0 to 5.2 and caprylate ion concentration of about 15 mM to about 60 mM.*

*10. A method of preparing a purified, virally inactivated immunoglobulin preparation from a starting material comprising immunoglobulin and other substances, the method comprising the steps of*

*(a) adjusting the starting material to conditions of pH, temperature, and sodium caprylate concentration such that a first precipitate and a first supernatant comprising immunoglobulin are formed,*

*(b) separating the first supernatant from the first precipitate,*

*(c) incubating the first supernatant under conditions of time, pH, temperature, and caprylate concentration to inactivate substantially all enveloped viruses, and such that a second precipitate and a second supernatant comprising immunoglobulin are formed, and*

*(d) separating the second supernatant from the second precipitate to produce a purified, virally inactivated immunoglobulin preparation.*

*11. The method of claim 10 wherein the conditions under which said first precipitate and first supernatant form comprise a pH within a range of from about 5.0 to about 5.2 and a sodium caprylate concentration within a range of about 15 mM to about 25 mM.*

*12. The method of claim 10 wherein the conditions under which substantially all enveloped viruses are inactivated and the second precipitate and second supernatant form comprise a pH within a range of about 5.0 to about 5.2, a caprylate concentration within a range of about 15 mM to about 40 mM, a temperature of about 25-35° C., and a period of time of about 15 minutes to about 6 hours.*

* * * * *